US008097764B2

(12) United States Patent
Brown et al.

(10) Patent No.: US 8,097,764 B2
(45) Date of Patent: Jan. 17, 2012

(54) METHODS OF ISOMERIZING XYLENES WITH A CATALYST REDUCED IN THE PRESENCE OF HYDROGEN AND A BASE

(75) Inventors: Scott H. Brown, Kingwood, TX (US); Tin-Tack Peter Cheung, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 12/940,291

(22) Filed: Nov. 5, 2010

(65) Prior Publication Data

US 2011/0046428 A1    Feb. 24, 2011

Related U.S. Application Data

(62) Division of application No. 11/959,872, filed on Dec. 19, 2007, now Pat. No. 7,851,664.

(51) Int. Cl.
*C07C 5/27* (2006.01)
*B01J 29/06* (2006.01)

(52) U.S. Cl. .......... 585/481; 585/482; 585/906; 502/60; 502/63; 502/64; 502/66; 502/77

(58) Field of Classification Search .................... 502/60, 502/63, 64, 66, 67, 71, 77; 585/481, 482, 585/906
See application file for complete search history.

(56) References Cited

U.S. PATENT DOCUMENTS

| | | | |
|---|---|---|---|
| 3,702,886 A | 11/1972 | Argauer et al. |
| 4,326,994 A | 4/1982 | Haag et al. |
| 4,374,296 A | 2/1983 | Haag et al. |
| 4,414,137 A | 11/1983 | Young et al. |
| 4,418,235 A | 11/1983 | Haag et al. |
| 4,469,909 A | 9/1984 | Chester et al. |
| 4,481,102 A | 11/1984 | Young et al. |
| 4,501,925 A | 2/1985 | Young et al. |
| 4,513,091 A | 4/1985 | Chang et al. |
| 4,513,158 A | 4/1985 | Young et al. |
| 4,524,140 A | 6/1985 | Chang et al. |
| 4,548,705 A | 10/1985 | Young et al. |
| 4,559,314 A | 12/1985 | Shihabi |
| 4,559,315 A | 12/1985 | Chang et al. |
| 4,618,738 A | 10/1986 | Young et al. |
| 4,621,161 A | 11/1986 | Shihabi |
| 4,626,609 A | 12/1986 | Shihabi |
| 4,638,105 A | 1/1987 | Chang et al. |
| 4,642,404 A | 2/1987 | Shihabi |
| 4,910,006 A | 3/1990 | Zones et al. |
| 5,095,169 A | 3/1992 | Skeels et al. |
| 5,225,179 A | 7/1993 | Zones et al. |
| 5,258,570 A | 11/1993 | Skeels et al. |
| 5,316,753 A | 5/1994 | Nakagawa |
| 5,393,718 A | 2/1995 | Skeels et al. |
| 5,659,099 A | 8/1997 | Skeels et al. |
| 5,744,673 A | 4/1998 | Skeels et al. |
| 5,763,348 A * | 6/1998 | Fung et al. ........... 502/37 |
| 5,877,374 A | 3/1999 | Nacamuli et al. |
| 6,051,744 A | 4/2000 | Nacamuli et al. |
| 6,350,929 B2 | 2/2002 | Magne-Drisch et al. |
| 6,512,155 B1 | 1/2003 | Johnson et al. |
| 6,544,495 B1 | 4/2003 | Elomari |
| 6,555,080 B1 | 4/2003 | Elomari |
| 6,616,830 B2 | 9/2003 | Elomari |
| 6,616,911 B2 | 9/2003 | Elomari |
| 6,743,962 B2 | 6/2004 | O'Rear et al. |
| 6,768,035 B2 | 7/2004 | O'Rear et al. |
| 7,122,500 B2 | 10/2006 | Chang et al. |
| 7,253,331 B2 | 8/2007 | Martens et al. |
| 2005/0166581 A1 | 8/2005 | Davis et al. |
| 2009/0163752 A1 | 6/2009 | Brown et al. |

FOREIGN PATENT DOCUMENTS

| | | |
|---|---|---|
| CA | 1170281 | 7/1984 |
| CN | 1280975 A | 1/2001 |
| DE | 10030173 A1 | 1/2001 |
| ES | 2100277 | 6/1997 |
| FR | 2784686 A1 | 4/2000 |
| FR | 2795343 A1 | 12/2000 |
| JP | 56130233 A | 10/1981 |
| JP | 59010530 A | 1/1984 |
| SU | 243575 | 3/1972 |

OTHER PUBLICATIONS

Edison, R.R., et al., "New xylene isom process scores high," Oil and Gas Journal, 1979, 6 pages, PennWell Publishing Co.
Gajewski, Franciszek, et al., "Isomerization and disproportionation of m-xylene on hydrogen-cerium forms of X and Y zeloites," Przemysl Chemiczny, 1977, vol. 56, No. 12, pp. 638-640, Institute Chem. Technol. Org., Politech, Krakowska, Krakow, Poland.
Li, Zenghe, et al., "Kinetics for m-xylene isomerization over zeolite ZSM-5," Beijing Huagong Daxue Xuebao, Ziran Kexueban, 1997, vol. 24., No. 4, pp. 67-70, Beijing Huagong Daxue Xuebao Bianjibu, Peoples Republic of China.
Shirinskaya, L. P., et al., "Effect of hydrothermal treatment on the catalytic activity of ultrahigh-silica zeolites in m-xylene isomerization," Inst. Obshch. Neorg. Khim., Doklady Akademii Nauk, 1987, vol. 31, No. 5, pp. 445-447, Minsk, USSR.
Tsuchiya, Susumu, et al., "Catalytic isomerization of xylenes over aluminium bromide supported on carbon," Sekiyu Gakkaishu, 1986, vol. 29, No. 2, pp. 113-121, Japan.
Usov, Yu N., et al., "Isomerization of m-xylene on decationated mordenite," Neftekhimiya, 1973, vol. 13, No. 1, pp. 41-45, Saratov, USSR.
Wang, Qiuying, et al., "A catalysis study on the HY zeolite modified with Pt," Journal of Lanzhou University, 1990, vol. 26, No. 4, Lanzhou, China.
PL202257, Application PL 1977-202257, Polish patent information; 1 page.
Dockter, Terri A., Search Report, "Xylene Isomerization Catalyst and Process Using a N2/H2 or NH3/N2/H2 for Catalyst Activation," Aug. 4, 2003, 33 pages, Patent Research and Information Analysis.

* cited by examiner

*Primary Examiner* — Elizabeth Wood
(74) *Attorney, Agent, or Firm* — Conley Rose, P.C.; Rodney B. Carroll; Chad Walter

(57) ABSTRACT

A xylene isomerization process includes introducing gas comprising hydrogen and a base to a reaction zone in which a catalyst comprising a Group VIII metal and a zeolite support resides. In one embodiment, the base may be formed in situ within the reaction zone from nitrogen and hydrogen that are introduced to the reaction zone. In another embodiment, the base is introduced directly to the reaction zone. The conditions in the reaction zone are effective to reduce the catalyst. A stream comprising $C_8$ aromatics, e.g., xylenes and ethylbenzene may then be fed to the reaction zone containing the reduced catalyst. The reaction zone may be operated at conditions effective to isomerize the xylenes and hydrodealkylate the ethylbenzene. The xylene loss during the isomerization of the xylenes is lowered as a result of using the catalyst reduced in the presence of the gas comprising a base and hydrogen.

20 Claims, No Drawings

METHODS OF ISOMERIZING XYLENES WITH A CATALYST REDUCED IN THE PRESENCE OF HYDROGEN AND A BASE

CROSS-REFERENCE TO RELATED APPLICATIONS

This is a Divisional Application of U.S. patent application Ser. No. 11/959,872, filed Dec. 19, 2007 and published as U.S. 2009/0163752A1, and entitled "Methods of Isomerizing Xylenes with a Catalyst Reduced in the Presence of Hydrogen and a Base," which is hereby incorporated by reference herein in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present invention generally relates to xylene isomerization catalysts and methods of making and using same, and more particularly to isomerization of xylenes with a catalyst that has been reduced in the presence of hydrogen and a base.

BACKGROUND OF THE INVENTION

The xylene isomers orthoxylene, metaxylene, and paraxylene, are important chemical intermediates. Orthoxylene may be oxidized to make phthalic anhydride, which is used to make phthalate-based plasticizers among other things. Metaxylene may be oxidized to make isophthalic acid, which is used in unsaturated polyester resins. Paraxylene may be oxidized to make terephthalic acid, which in turn is used to make polymers such as polytrimethyleneterephthalate, polybutyleneterephthalate (PBT), and polyethyleneterephthalate (PET). PET is one of the largest volume polymers in the world and is used to make PET plastics (e.g., two liter PET bottles). It is also used to make polyester fiber, which in turn is used to make clothes and other fabrics. Given the large market for PET plastics and fibers, there is a substantial demand for high purity paraxylene, which is several times larger than the demand for orthoxylene and metaxylene. To help meet such demand, orthoxylene and metaxylene may be isomerized to paraxylene via use of an isomerization catalyst.

Paraxylene may be produced by reforming or aromatizing a wide boiling range naphtha in a reformer, for example, a Continuous Catalytic Reformer (CCR) or semi-regenerative reformer, followed by distillation of the naphtha reformer effluent into a $C_8$ aromatics fraction (containing aromatics having eight carbon atoms). This $C_8$ aromatics fraction comprises near equilibrium amounts of orthoxylene, metaxylene, and paraxylene along with ethylbenzene. The paraxylene is separated from the other components in this $C_8$ aromatics fraction in a separation unit either by a crystallization process or by an adsorption process, thereby forming a paraxylene-depleted stream. The paraxylene-depleted stream may be further processed by passing it over a xylene isomerization catalyst in a xylene isomerization unit, wherein orthoxylene and metaxylene are isomerized to paraxylene.

Xylene isomerization catalysts may comprise a ZSM-5 zeolite support. However, these catalysts have some unwanted side reactions that consume the xylene isomers and reduce the overall xylene selectivity. Such side reactions are particularly a problem when the catalyst is of the HZSM-5 type, wherein H refers to the ZSM-5 being predominately in the hydrogen form. The HZSM-5 catalyst has several acid sites that promote unwanted cracking reactions, resulting in a relatively high amount of xylene loss and thus a decrease in the production of paraxylene. A need therefore exists to reduce the xylene losses that occur during the xylene isomerization process such that the overall xylene selectivity and thus the production of paraxylene is increased.

SUMMARY OF THE INVENTION

Methods of isomerizing xylenes include introducing hydrogen and a base to a reaction zone in which a catalyst comprising a Group VIII metal and a zeolite support resides. The conditions in the reaction zone are desirably effective to reduce the catalyst in the presence of the base and the hydrogen. In one embodiment, the base may be formed in situ within the reaction zone from nitrogen ($N_2$) and hydrogen ($H_2$) that are introduced to the reaction zone. In another embodiment, the base is introduced directly to the reaction zone and may comprise, for example, ammonia ($NH_3$), alkyl amines, hydrazine, or combinations thereof. A stream comprising $C_8$ aromatics, e.g., xylenes and ethylbenzene, may then be fed to the reaction zone containing the reduced catalyst. The reaction zone may be operated at conditions effective to isomerize the xylenes and hydrodealkylate the ethylbenzene. Reducing the catalyst in the presence of the hydrogen and the base decreases the xylene loss during the isomerization of the xylenes.

DETAILED DESCRIPTION OF THE PREFERRED EMBODIMENTS

Disclosed herein are xylene isomerization catalysts comprising a HZSM-5 zeolite support, a SSZ-57 zeolite support, or both and one or more Group VIII metals. The xylene isomerization catalysts may be activated by reduction in the presence of hydrogen and a base. The reduced catalysts may be used for the isomerization of xylenes.

The xylene isomerization catalyst may comprise a HZSM-5 zeolite support. HZSM-5 zeolite refers to ZSM-5 zeolite that is predominantly in the hydrogen form, meaning that the ZSM-5 zeolite is in an acidic form as opposed to a basic form. A basic form is one where the ZSM-5 zeolite has substantial amounts of the original sodium, i.e., the sodium that is present in the as-synthesized ZSM-5 zeolite. The HZSM-5 zeolite may be formed by replacing most of the original cations of the ZSM-5 zeolite with hydrogen using methods known in the art such as subjecting the ZSM-5 zeolite to an ion exchange with ammonium salts followed by calcination. Examples of suitable salts include but are not limited to chlorides, nitrates, sulfates, acetates, carbonates and combinations thereof. The HZSM-5 zeolite may have greater than or equal to about 80% of the sodium ions replaced by hydrogen ions, alternatively greater than or equal to about 90%, alternatively greater than or equal to about 95%, or alternatively greater than or equal to about 98%. In accordance with these replacements, the amount of sodium remaining in the HZSM-5 zeolite will depend on the original amount present, which in turn will depend on factors such as the silica to alumina ratio. Keeping these qualifications in mind, the amount of sodium left in the HZSM-5 zeolite after it has been converted to the hydrogen form may be less than about 0.1%, alternatively less than about 0.06%, or alternatively less than about 0.03%, all percentages being by weight of the original sodium.

The HZSM-5 zeolite may be employed in a "bound" form, i.e., with a refractory oxide as a binder for the overall catalyst particle. The binder serves to hold the crystalline zeolite particles together in a catalyst particle of suitable size and suitable attrition resistance upon handling and use in the isomerization process. Examples of suitable refractory oxide binders include alumina, silica, titania, clay, or mixtures thereof. A suitable commercially available binder is CATAPAL®-B binder, which may be purchased from Sasol. The amount of binder used may be in a range of from about 5% to about 65%, alternatively from about 10% to about 50%, all percentages being by weight of the HZSM-5 zeolite.

The HZSM-5 zeolite may have a relatively small crystal size. In embodiments, the crystal size of the HZSM-5 zeolite is less than about 1.0 micron, alternatively less than about 0.9 micron, alternatively in a range of from about 0.2 micron to about 0.9 micron, or alternatively in a range of from about 0.2 micron to about 0.8 micron. The HZSM-5 zeolite may have pore sizes or diameters in the range of from about 5 Angstroms to about 7 Angstroms, alternatively about 5.5 Angstroms. Zeolites with these pore sizes are commonly referred to as "intermediate pore size zeolites", and are in contrast to the larger pore size zeolites such as faujasite or the smaller pore size zeolites such Linde Type A and erionite. The structure of HZSM-5 zeolites is described by Kokotailo et al. in Nature, Vol. 272, Mar. 30, 1978, page 437, which is incorporated by reference herein in its entirety. The pore size of the crystalline zeolite is delineated by the atomic structure. However, the pore size may be modified by components added to the HZSM-5 zeolite.

The HZSM-5 zeolite can be prepared in various manners. Suitable preparation procedures are described in U.S. Pat. No. 3,702,886, which is incorporated by reference herein in its entirety. In an embodiment, the HZSM-5 zeolite can be made by preparing a solution containing water, tetrapropyl ammonium hydroxide and the elements of sodium oxide, an oxide of aluminum or gallium, and an oxide of silica such that the solution has the following composition in terms of mole ratios of oxides:

TABLE 1

|  | Broad Range | Intermediate Range | Narrow Range |
|---|---|---|---|
| OH$^-$/SiO$_2$ | 0.07-1.0 | 0.1-0.8 | 0.2-0.75 |
| R$_4$N+/(R$_4$N$^+$+ Na$^+$) | 0.2-0.95 | 0.3-0.9 | 0.4-0.9 |
| H$_2$O/OH$^-$ | 10-300 | 10-300 | 10-300 | wherein R is propyl.

The broad, intermediate, and narrow ranges are different embodiments of the mole ratios. In embodiments, the silica/alumina ratio of the ZSM-5 zeolite is in a range of from about 10 to about 300, from about 30 to about 200, from about 30 to about 150, from about 50 to about 100, and from about 70 to about 90. The mixture may be maintained at reaction conditions until the crystals of the zeolite are formed. Thereafter, the crystals may be separated from the liquid and recovered. Typical reaction conditions include a temperature in a range of from about 160° F. to about 400° F. for a period of from about 2 days to about 60 days, or alternatively a temperature in a range of from about 190° F. to about 235° F. for a period of from about 7 days to about 21 days. The solid product may be separated from the reaction medium by cooling it to room temperature, filtering it, and washing it with water. The as-synthesized ZSM-5 zeolite may be further converted from a basic to an acidic form, as described previously, to provide the HZSM-5 zeolite that may be used as a support for one or more catalytic metals selected from the Group VIII metals of the periodic table.

The xylene isomerization catalyst may comprise a SSZ-57 zeolite support. SSZ-57 refers to a zeolite that can be prepared as described herein in both the borosilicate or aluminosilicate phase. The term "borosilicate" refers to a zeolite containing oxides of both boron and silicon. The term "aluminosilicate" refers to a zeolite containing oxides of both aluminum and silicon. In preparing SSZ-57 zeolites, a N-cyclohexyl-N-butylpyrrolidinium ammonium cation, N-propyl-N-cycloheptylpyrrolidinium cation or N-butyl-N-cyclooctylpyrrolidinium may be used as a templating agent. In general, SSZ-57 may be prepared by contacting an active source of an oxide selected from silicon oxide, germanium oxide and mixtures thereof and boron oxide or a combination of boron oxide and aluminum oxide, gallium oxide, indium oxide, titanium oxide or a mixture thereof with the templating agent. In an embodiment, SSZ-57 may be prepared from a reaction mixture comprising the following mole ratios of reagents: YO$_2$/WaO$_b$ from about 20 to ∞, OH$^-$/YO$_2$ from about 0.1 to about 0.5, Q/YO$_2$ from about 0.05 to about 0.5, M$_{2/n}$/YO$_2$ from about 0.02 to about 0.4 and H$_2$O/YO$_2$ from about 25 to about 80 wherein Y is silicon, germanium or a mixture thereof; W is boron or a combination of boron and aluminum, gallium, indium, titanium or a mixture thereof; M is an alkali metal cation, alkaline earth metal cation or mixtures thereof; n is the valence of M (i.e., 1 or 2); a is 1 or 2; b is 2 when a is 1 (i.e., W is tetravalent) or b is 3 when a is 2 (i.e., W is trivalent); and Q comprises a N-butyl-N-cyclohexylpyrrolidinium cation, N-propyl-N-cycloheptylpyrrolidinium cation or N-butyl-N-cyclooctylpyrrolidinium cation. Alternatively, SSZ-57 may be prepared from a reaction mixture comprising the following mole ratios of reagents: YO$_2$/WaO$_b$ from about 35 to 90, OH$^-$/YO$_2$ from about 0.2 to about 0.3, Q/YO$_2$ from about 0.1 to about 0.2, M$_{2/n}$/YO$_2$ from about 0.1 to about 0.25 and H$_2$O/YO$_2$ from about 30 to about 50.

In practice, SSZ-57 is prepared by a process comprising: (a) preparing an aqueous solution containing sources of at least one oxide capable of forming a crystalline molecular sieve and the N-butyl-N-cyclohexylpyrrolidinium cation, N-propyl-N-cycloheptylpyrrolidinium cation or N-butyl-N-cyclooctylpyrrolidinium cation in the presence of an anionic counterion which is not detrimental to the formation of SSZ-57; (b) maintaining the aqueous solution under conditions sufficient to form crystals of SSZ-57; and (c) recovering the crystals of SSZ-57. Accordingly, SSZ-57 may comprise the crystalline material and the templating agent in combination with metallic and non-metallic oxides bonded in tetrahedral coordination through shared oxygen atoms to form a cross-linked three dimensional crystal structure. The metallic and non-metallic oxides comprise an oxide selected from silicon oxide, germanium oxide and mixtures thereof and boron oxide or a combination of boron oxide and aluminum oxide, gallium oxide, indium oxide, titanium oxide or a mixture thereof. Typical sources of silicon oxide include silicates, silica hydrogel, silicic acid, fumed silica, colloidal silica, tetra-alkyl orthosilicates, and silica hydroxides. Boron, as well as aluminum, gallium, germanium, titanium, and indium can be added in forms corresponding to their silicon counterparts.

A source zeolite reagent may provide a source of boron. In most cases, the source zeolite also provides a source of silica. The source zeolite in its dealuminated or deboronated form may also be used as a source of silica, with additional silicon added using, for example, the conventional sources listed above. Use of a source zeolite reagent as a source of alumina for the preparation of a SSZ-57 zeolite support is more completely described in U.S. Pat. No. 5,225,179, issued Jul. 6, 1993 to Nakagawa entitled "Method of Making Molecular Sieves," the disclosure of which is incorporated herein by reference.

An alkali metal hydroxide and/or an alkaline earth metal hydroxide, such as the hydroxide of sodium, potassium, lithium, cesium, rubidium, calcium, and magnesium, may be used in the reaction mixture; however, this component can be omitted so long as the equivalent basicity is maintained. The templating agent may be used to provide hydroxide ion. Thus, it may be beneficial to ion exchange, for example, the halide for hydroxide ion, thereby reducing or eliminating the alkali metal hydroxide quantity required. The alkali metal cation or alkaline earth cation may be part of the as-synthesized crystalline oxide material, in order to balance valence electron charges therein.

In an embodiment, the reaction mixture is maintained at an elevated temperature until the crystals of the SSZ-57 zeolite are formed. The hydrothermal crystallization may be conducted under autogenous pressure, at a temperature between 100° C. and 200° C., alternatively between 135° C. and 160° C. The crystallization period may be greater than about 1 day, alternatively from about 3 days to about 20 days. In an embodiment, the zeolite is prepared using mild stirring or agitation. During the hydrothermal crystallization step, the SSZ-57 crystals can be allowed to nucleate spontaneously from the reaction mixture. The use of SSZ-57 crystals as seed material can be advantageous in decreasing the time necessary for complete crystallization to occur. In addition, seeding can lead to an increased purity of the product obtained by promoting the nucleation and/or formation of SSZ-57 over any undesired phases. When used as seeds, SSZ-57 crystals are added in an amount between 0.1 and 10% of the weight of silica used in the reaction mixture. Once the zeolite crystals have formed, the solid product may be separated from the reaction mixture by standard mechanical separation techniques such as filtration. The crystals may then be water-washed and dried, e.g., at 90° C. to 150° C. for from about 8 to about 24 hours, to obtain the as-synthesized SSZ-57 zeolite crystals. The drying step can be performed at atmospheric pressure or under vacuum.

SSZ-57, prepared as described herein, has a mole ratio of an oxide selected from silicon oxide, germanium oxide and mixtures thereof to boron oxide or a combination of boron oxide and aluminum oxide, gallium oxide, indium oxide, titanium oxide or a mixture thereof greater than about 20; and has the X-ray diffraction lines of Table 2. SSZ-57 further has a composition, as-synthesized and in the anhydrous state, in terms of mole ratios, shown in Table 3.

TABLE 2

| As synthesized SSZ-57 | | |
|---|---|---|
| Two Theta (deg)[a] | d-spacing | Intensity $I/I_o$[b] |
| 7.7 | 11.5 | S |
| 8.8 | 10.0 | M |
| 14.65 | 6.04 | W |
| 15.55 | 5.69 | W |
| 17.65 | 5.02 | W |
| 20.85 | 4.26 | W |
| 23.05 | 3.86 | VS |

TABLE 2-continued

| As synthesized SSZ-57 | | |
|---|---|---|
| Two Theta (deg)[a] | d-spacing | Intensity $I/I_o$[b] |
| 24.35 | 3.65 | M |
| 26.6 | 3.35 | W |
| 30.2 | 2.96 | W |
| 45.1 | 2.10 | W |

[a]±0.15
[b]The X-ray patterns provided are based on a relative intensity scale in which the strongest line in the X-ray pattern is assigned a value of 100. W(weak) is less than 20; M(medium) is between 20 and 40; S(strong) is between 40 and 60; VS(very strong) is greater than 60.

TABLE 3

| As synthesized SSZ-57 | |
|---|---|
| $YO_2/W_cO_d$ | 20-∞ |
| $M_{2/n}/YO_2$ | 0.01-0.03 |
| $Q/YO_2$ | 0.02-0.05 | where Y, W, c, d, M and Q are as defined previously.

SSZ-57 can be made essentially aluminum free, i.e., having a silica to alumina mole ratio approaching infinity. A method of increasing the mole ratio of silica to alumina is by using standard acid leaching or chelating treatments. However, essentially aluminum-free SSZ-57 can be synthesized directly using essentially aluminum-free silicon and boron sources. SSZ-57 is generally prepared directly as a borosilicate. Lower silica to alumina ratios may also be obtained by using methods which insert aluminum into the crystalline framework. For example, aluminum insertion may occur by thermal treatment of the zeolite in combination with an alumina binder or dissolved source of alumina. Such procedures are described in U.S. Pat. No. 4,559,315, issued on Dec. 17, 1985 to Chang et al., incorporated by reference herein in its entirety. It is believed that SSZ-57 is comprised of a new framework structure or topology which is characterized by its X-ray diffraction pattern. SSZ-57 zeolites, as-synthesized, have a crystalline structure whose X-ray powder diffraction pattern exhibit the characteristic lines shown in Table 2 and is thereby distinguishable from other zeolites.

Crystalline SSZ-57 can be used as-synthesized, but may be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica to alumina mole ratio. The zeolite can also be steamed; steaming helps stabilize the crystalline lattice to attack from acids.

SSZ-57 can be formed into a wide variety of physical shapes. Generally speaking, the zeolite can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or dried or partially dried and then extruded. SSZ-57 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety. Methods of preparing and utilizing SSZ-57 catalysts have been disclosed in U.S. Pat. Nos. 6,544,495 and 6,616,830, both of which are incorporated by reference herein.

The xylene isomerization catalyst may further comprise one or more Group VIII metals such as platinum (Pt), palladium (Pd), nickel (Ni), cobalt (Co), rhodium (Rh), iridium (Ir), iron (Fe), ruthenium (Ru), osmium (Os), or combinations thereof. Alternatively, the catalyst may comprise platinum, palladium, nickel or combinations thereof. The metal is believed to act as a hydrogenation/dehydrogenation component. In an embodiment in which the Group VIII metal is Pt, the amount of Pt present on the catalyst may be in a range of from about 0.05% to about 1.0%, alternatively from about 0.05% to about 0.75%, or alternatively from about 0.075% to about 0.5%, all percentages being by total weight of the catalyst. In an embodiment in which the Group VIII metal is Pd, the amount of Pd present in the catalyst may be in a range of from 0.1% to 2.0%, alternatively from about 0.1% to about 1.5%, or alternatively from about 0.15% to about 1.0%, all percentages being by total weight of the catalyst. In an embodiment in which the Group VIII metal is Ni, the amount of Ni present in the catalyst may be in a range of from about 0.1% to about 20%, alternatively from about 0.1% to about 10%, or alternatively from about 1% to about 8%. Mixtures of Group VIII metals can also be used in conjunction with the SSZ-57 zeolite. Mixtures such as Pt and Ni; Pt and Pd; Pd and Ni; and Pt, Pd, and Ni can be used in numerous different proportions to achieve a suitable catalyst.

The Group VIII metal may be added to the zeolite support by any suitable method known in the art. For example, the metal may be added to the zeolite support by ion-exchange or by impregnation. In general, the metals are added as salts, by filling the pores of the catalyst with a solution of appropriate concentration to achieve the desired metal loading. The metals may be added as salts, for example as salts of thermally decomposable anions such as for example the nitrate, nitrite or, acetate salt. Alternatively, the metals may be added as soluble metal complexes. Following addition of the metal to the zeolite support, the mixture may be equilibrated, dried, and calcined to decompose the salts or soluble complexes, remove solvent, remove impurities and/or to remove volatile products. Alternatively, adsorption or other techniques well known in the art for introducing metals into porous substances may also be used.

The xylene isomerization catalysts may be activated by reduction in the presence of hydrogen and a base. The xylene isomerization catalysts may be placed in a suitable reaction zone, for example a reactor vessel, where the catalyst may be subjected to a reducing atmosphere. The reaction zone may be heated while carrying out the catalyst reduction. The catalyst may be optionally dehydrated in an inert gas such as nitrogen before reduction in the presence of hydrogen and the base. In an embodiment, the catalyst is dehydrated in the presence of hydrogen and a base wherein hydrogen may be present in an amount equal to or less than about 100 vol. %. Additionally or alternatively, the reduction with hydrogen and the base may be carried out in the presence of nitrogen. Where nitrogen is present, the amount of hydrogen in the reducing atmosphere may range from about 1 to about 50 vol. %, alternatively from about 5 to about 35 vol. %, alternatively from about 5 to about 25 vol. %, alternatively from about 10 to about 25 vol. %, or alternatively from about 10 to about 20 vol. %, based upon the total volume of hydrogen and nitrogen present in the reaction zone. Thus, the reducing atmosphere may comprise a base, hydrogen, and optionally an inert gas such as nitrogen. The amount of base introduced to the reaction zone may be a trace amount, for example an amount in a range of from about 1 ppmv to about 10,000 ppmv, alternatively from about 5 ppmv to about 1000 ppmv, or alternatively, from about 10 ppmv to about 500 ppmv by total volume of the hydrogen and the inert gas.

In an embodiment, a base is fed into the reaction zone. Suitable bases can comprise ammonia, alkyl amines (R'R"R'"N; wherein R', R", and R'" can be alkyl radicals from 1 to 5 carbon atoms), hydrazine ($H_2NNH_2$), or combinations thereof. In another embodiment, all or a portion of the base may be introduced to the reaction zone by forming the base in situ within the reaction zone. Nitrogen and hydrogen may be introduced to the reaction under reaction conditions sufficient to form the base, i.e., ammonia. In an embodiment, the nitrogen and hydrogen may be introduced to the reaction in amounts and under conditions sufficient to form trace amounts of ammonia. Alternatively, the nitrogen and hydrogen may be introduced to the reactor in the amounts set forth previously.

The reduction may be carried out at reaction conditions to reduce the Group VIII metal, to form the base in situ within the reaction zone, or both. In an embodiment, the reduction is performed at a temperature of from about 500 to about 1500° F., alternatively from about 600 to about 1200° F., alternatively from about 700 to about 950° F.; a pressure of from about 0.5 to about 10 atm, alternatively from about 1 to about 5 atm; a gas hourly space velocity (GHSV) of from about 10 to about 5000 $hr^{-1}$, alternatively from about 500 to about 2000 $hr^{-1}$; and from about 1 to about 100% hydrogen, alternatively from about 5 to about 25% hydrogen based on the total volume of hydrogen and nitrogen present in the reaction zone.

The reduced xylene isomerization catalyst may be used in a xylene isomerization/ethylbenzene hydrodealkylation process, which may be simply referred to as a "xylene isomerization process." A xylene isomerization unit typically serves at least two functions. First, it re-equilibrates the xylenes portion of a paraxylene-depleted stream by forming paraxylene from the xylene isomers orthoxylene and metaxylene. As used herein, "paraxylene-depleted stream" refers to a stream containing a below equilibrium level of paraxylene relative to the other xylenes (orthoxylene and metaxylene) in the stream. Second, it transalkylates or hydrodealkylates the ethylbenzene in the paraxylene-depleted stream to facilitate its removal from the $C_8$ aromatics fraction. Since ethylbenzene boils in the same range as the xylene isomers, it is more economical to include it in the $C_8$ aromatics fraction that is fed to the paraxylene separation process than attempt recovery by distillation. As a result of the xylene isomerization reaction, paraxylene is formed from the other components of the paraxylene-depleted stream. Moreover, due to the selectivity of the catalyst for paraxylene, more than an equilibrium amount of paraxylene is produced. Additional teaching regarding xylene isomerization may be found in U.S. Pat. Nos. 6,051,744 and 5,877,374, each of which is incorporated by reference herein in its entirety.

Ethylbenzene is normally not removed with the paraxylene in the crystallization or adsorption step; moreover it is not efficiently isomerized under the xylene isomerization conditions generally employed. Thus, it is highly desirable to remove as much ethylbenzene as possible per pass by transalkylation or hydrodealkylation so that the ethylbenzene does not accumulate in the recycle loop. If this accumulation were to occur, a bleed stream out of the paraxylene production loop would be necessary to remove the ethylbenzene, which would reduce paraxylene production. Thus, a function of the isomerization unit is to react-out the ethylbenzene by simple dealkylation, hydrodealkylation, isomerization, or transalkylation/disproportionation, depending on the type of isomerization process. As noted previously, the conversion of ethylbenzene and the isomerization of orthoxylene and metaxylene are referred to collectively herein as xylene isomerization.

A xylene isomerization catalyst which is effective in removal of ethylbenzene can to a much smaller extent catalyze side reactions that lead to the destruction of the desired xylene product. There are numerous side reactions leading to the destruction of xylene. Such reactions include without limitation transalkylations and disproportionation reactions such as shown in Equations 1-3:

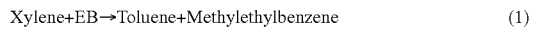
$$Xylene + EB \rightarrow Toluene + Methylethylbenzene \quad (1)$$

$$Xylene + EB \rightarrow Benzene + Dimethylethylbenzene \quad (2)$$

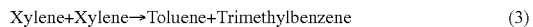
$$Xylene + Xylene \rightarrow Toluene + Trimethylbenzene \quad (3)$$

where EB represents ethylbenzene. The optimization of a xylene isomerization catalyst may entail the maximization of EB conversion while simultaneously minimizing the loss of xylene via reactions such as those given in Equations 1-3. In an embodiment, a xylene isomerization catalyst of this disclosure may function to maximize the overall xylene selectivity by minimizing the loss of xylene. Herein, the xylene selectivity may be may expressed as the mole ratio of ethylbenzene conversion to the xylene loss (EB/XL). In an embodiment, the xylene isomerization catalyst of this disclosure has an EB/XL of from about 70 to about 600, alternatively from about 100 to about 450, alternatively from about 150 to about 350.

Xylene isomerization may be performed by contacting the reduced xylene isomerization catalyst with a paraxylene-depleted stream in an isomerization reaction zone under suitable reaction conditions such that one or more components of the paraxylene-depleted stream undergo xylene isomerization as described herein. In an embodiment, the isomerization reaction zone is the same as the reduction reaction zone. For example, the xylene isomerization catalyst may be loaded into a reactor vessel, reduced in situ, and subsequently contacted with a paraxylene-depleted stream for isomerization thereof.

The paraxylene-depleted stream for the xylene isomerization process may be obtained from a paraxylene separation unit comprising an adsorption process, a crystallization process, or a combination thereof. Such processes remove paraxylene from a $C_8$ aromatics fraction, thereby forming a paraxylene-depleted stream. The $C_8$ aromatics fraction may be obtained from reforming or aromatizing a wide boiling range naphtha in a reformer, for example a continuous catalytic reformer (CCR) or semi-regenerative reformer, which contains near equilibrium amounts of orthoxylene, metaxylene, and paraxylene, along with ethylbenzene. In embodiments, the amount of paraxylene present in the paraxylene-depleted stream may be in a range of from about 0% to about 20%, alternatively from about 0% to about 12%, by total weight of the stream. A paraxylene-depleted stream that is obtained predominantly from a paraxylene separation unit that comprises an adsorption process will typically have lower amounts of paraxylene than a paraxylene-depleted stream that is obtained from a paraxylene separation unit based on a crystallization process. The paraxylene-depleted stream may also have an ethylbenzene concentration in a range of from about 5% to about 25%, alternatively from about 10% to about 20%, alternatively from about 9% to about 12%, by weight of the stream. The paraxylene-depleted stream may have a small concentration of non-aromatic compounds in a range of from about 0% to about 15%, alternatively from about 0% to about 8%, alternatively from about 0% to about 5%, by weight of the stream. The balance of the paraxylene-depleted stream comprises mixed xylenes.

The xylene isomerization may be carried out at a relatively low pressure under a relatively low flow of hydrogen, commonly referred to as a "trickle flow" of hydrogen. The trickle flow of hydrogen typically passes through the isomerization reaction zone in which the catalyst resides once and thus no hydrogen recycle occurs. The hydrogen may be fed to the isomerization reaction zone at a rate such that the mole ratio of hydrogen to ethylbenzene ranges from about 1.0 to about 7.0, alternatively from about 1.0 to about 3.0. The hydrogen may be fed to the isomerization reaction zone at a rate such that the ratio of moles of total hydrocarbon to moles of hydrogen ranges from about 0.01 to about 1, alternatively from about 0.02 to about 0.45, alternatively from about 0.05 to about 0.25. The temperature in the isomerization reaction zone may range from about 500° F. to about 1000° F., alternatively from about 600° F. to about 900° F.

In an embodiment, the xylene isomerization is carried out using catalyst comprising a SSZ-57 support and Group VIII metal such as for example platinum and this mixture is hereafter referred to as Pt/SSZ-57. In such an embodiment, the Pt/SSZ-57 may function as a dual catalyst that is effective for the isomerization of mixed xylenes and the hydrodealkylation of ethylbenzene. Such a catalyst may be pretreated with ammonia as has been described herein. In an embodiment, the Pt/SSZ-57 is used as a catalyst in a trickle-hydrogen type process as previously described herein. In such an embodiment, the reaction may be carried out at a hydrogen pressure of less than about 50 psig and at a ratio of about 1.2 mole hydrogen per mole of ethylbenzene in the feed. Such processes may be advantageous in reactors wherein hardware limitations prevent the operation of the reactor at elevated pressures. Alternatively, the Pt/SSZ-57 catalyst may be used in a xylene isomerization process carried out at a high hydrogen pressure. In such an embodiment, the hydrogen pressure may range from about 50 psig to about 500 psig with about a 1-5:1 hydrogen/hydrocarbon ratio. Such processes may be advantageous in reactors designed for high pressure operation.

The xylene isomerization may be carried out in any suitable process equipment, for example a moving bed or fixed bed reactor. After reaching the end of a reaction cycle in a moving bed reactor, the catalyst may be regenerated in a regeneration section/zone where coke is burned off of the catalyst in an oxygen-containing atmosphere such as air at a relatively high temperature. The catalyst may then be recycled to the reaction zone for further contact with the feed. In a fixed bed reactor, the catalyst may be regenerated by using an inert gas containing a small amount of oxygen, e.g., from about 0.1 vol. % to about 2.0 vol. % by total volume of the gas, to burn the coke off of the catalyst in a controlled manner so as not to exceed a maximum temperature of about 950° F.

A reduced xylene isomerization catalyst as described herein may produce a greater than equilibrium amount of paraxylene as demonstrated by an initial PXATE (Paraxylene Approach to Equilibrium) of greater than about 100%, wherein PXATE=100*{(wt % of total xylenes that are $PX)_{product}$ −(wt % of total xylenes that are $PX)_{feed}$}/{(wt % of total xylenes that are $PX)_{equilibrium}$ −(wt % of total xylenes that are $PX)_{feed}$}, where the term (wt % of total xylenes that are $PX)_{equilibrium}$ is estimated from published temperature-dependant xylene equilibrium data, and is about 24 wt %. The catalyst also typically illustrates excellent stability from a paraxylene selectivity standpoint as demonstrated by a very slow decline in the PXATE with time. A slow decline in PXATE allows the cycle time between catalyst regenerations to be increased and effectively decreases the overall aging rate of the catalyst.

A reduced xylene isomerization catalyst as described herein may exhibit excellent stability from an ethylbenzene conversion standpoint. A portion of the ethylbenzene in the paraxylene-depleted stream may be converted by hydrodealkylation to, for example, benzene and ethane. Ethylbenzene conversion may be calculated as $EBConv=100*(wt\% EB_{feed}-wt\% EB_{prod})/wt\% EB_{feed}$. The EBConv may range from about 10 wt % to about 80 wt %, alternatively from about 20 wt % to about 75 wt %, or alternatively from about 25 wt % to about 70 wt %. Stoichiometrically, one mole of hydrogen is required to hydrodealkylate one mole of ethylbenzene. However, in practice, more hydrogen is required since all of the hydrogen does not react and some of the hydrogen reacts with molecules other than ethylbenzene. For example, the hydrogen may be used in hydrogenating cracked paraffins in the reaction zone. The hydrogen may also saturate some of the aromatic rings. In an embodiment, about 1.2 moles of hydrogen are present for every mole of ethylbenzene.

The reduced xylene isomerization catalyst may be regenerated as needed. As a catalytic process continues over time, the catalyst activity generally decreases. To offset a decrease in activity, other process conditions may be adjusted to compensate for the decrease, for example by increasing reactor temperature. When the catalyst activity and/or process conditions reach a point where the process is no longer efficiently catalyzed, the catalyst may need to be regenerated, if possible. Regeneration of the reduced isomerization catalyst may be needed when the ethylbenzene conversion becomes unacceptably low, when the non-aromatic conversion becomes unacceptably low, when the reaction temperature becomes unacceptably high, or combinations thereof.

A reduced xylene isomerization catalyst as described herein may reduce the xylene loss that occurs during the isomerization. As used herein, xylene loss ("XylLoss") refers to the percentage of the xylene isomers lost to hydrodealkylation and other processes, and is calculated by the equation, wherein $XylLoss=100*[(total\ wt\%\ xylenes)_{feed}-(total\ wt\%\ xylenes)_{product}]/(total\ wt\%\ xylenes)_{feed}$. The XylLoss during a continuous xylene isomerization run over a period of about 24 hours may range from about 0.0 wt % to about 5.0 wt %, alternatively from about 0.1 wt % to about 3.0 wt %, alternatively from about 0.2 wt % to about 2.0 wt %, alternatively from about 0.2 wt % to about 1.0 wt %, or alternatively from about 0.8 wt % to about 1.2 wt % by weight of the xylenes when the ethylbenzene conversion is about 50 wt %. Further, a xylene loss during a continuous run of the isomerization of the xylenes over a period of about 4 weeks may be in a range of from about 0.3 wt % to about 0.5 wt % by weight of the xylenes when the ethylbenzene conversion is about 50 wt %.

Without intending to be limited by theory, it is believed that the addition of the base during reduction of the xylene isomerization catalyst serves to hinder the reaction rate and number of unwanted side reactions that would otherwise occur during the isomerization. In particular, the base may adsorb on the acid sites of the zeolite where it typically bonds with the more reactive, stronger acid sites and desorbs from the weaker acid sites. As such, the base may selectively passivate a portion of the acid sites while leaving the other acid sites intact. It is believed that the stronger acid sites are disproportionately passivated. Those passivated acid sites are no longer free to react with the xylene isomers, and thus a reduced xylene loss is observed at a constant ethylbenzene conversion.

EXAMPLES

The invention having been generally described, the following examples are given as particular embodiments of the invention and to demonstrate the practice and advantages thereof. It is understood that the examples are given by way of illustration and are not intended to limit the specification or the claims to follow in any manner. In the following examples, the data is presented for the first 1000 hours on stream (HOS) of the isomerization run.

Comparative Example 1

Xylene isomerization was carried out in a bench scale reactor using a xylene isomerization catalyst comprising 0.25 weight percent platinum on an HZSM-5 zeolite support. The HZSM-5 zeolite support further comprised 80 weight percent zeolite and 20 weight percent binder. The paraxylene-depleted stream comprised, in weight percent, from about 3 to about 10 wt % non-aromatic compounds, from about 8 to about 12 wt % ethylbenzene, from about 3 to about 5 wt % paraxylene, from about 51 to about 55 wt % metaxylene, and from about 23 to about 24 wt % orthoxylene. A 0.5-inch diameter stainless steel reactor vessel having a length of about 45 inches was loaded with 53 grams of the catalyst, resulting in a catalyst volume of about 73 cc and a catalyst bed height of about 7 inches. The catalyst was dried in the reactor by feeding nitrogen to the reactor at 1.4 L/min and 25 psig. The reactor temperature was ramped at 25° F./hr from ambient temperatures to 500° F. and held at 500° F. until the water content of the reactor effluent dropped below 100 ppm. After drying, the catalyst was reduced by replacing the nitrogen flow to the reactor with hydrogen at 1.4 L/min and 75 psig. The reduction temperature was ramped from 500 to 800° F. at 10° F./hr, and held at 800° F. for fourteen hours before being allowed to cool to 625° F. They hydrogen flow rate was then reduced to 76 cc/min and the reactor pressure was reduced to 35 psig. The paraxylene-depleted stream (dried using 4 A molecular sieves) was then fed to the reactor at 225 gm/hr (260 cc/hr). The reactor was then operated at 625° F., 35 psig, and a weight hourly space velocity (WHSV) of 4.2 hr$^{-1}$ for 1 hour. The temperature was then ramped from 625° F. at 1° F./hr until 50 wt % ethylbenzene conversion was achieved, which normally occurred at about 640° F. The reactor effluent was sampled and tested via gas chromatograph, and the results are provided in Table 4 below.

Comparative Example 2

The catalyst used in Comparative Example 1 was regenerated in situ by flowing nitrogen at about 1200 cc/min mixed with enough air to provide an oxygen concentration of about 0.5 vol. % based on a total gas flow of about 1230-1240 cc/min, to the reactor at 70 psig and 500° F. After two hours the water content of the reactor effluent had dropped below 100 ppm, the reactor temperature was then ramped at 10° F./hr to 700° F. and held at 700° F. for 24 hours. Subsequently, the oxygen content was increased to 1.0 vol. % and the reactor was held at 700° F. for another 24 hours. Thereafter, the air flow was stopped, nitrogen was increased to 1.4 L/min, and the reactor was allowed to cool to 500° F. Subsequently, the regenerated catalyst was reduced and a paraxylene-depleted stream was introduced as described in Comparative Example 1. The results of the tests performed in this example are also shown in Table 4 below.

Example 1

The same procedure followed in Comparative Example 1 was performed with the exception that the dried catalyst was reduced in the presence hydrogen, nitrogen, and a base, i.e., ammonia. More specifically, a mixture of 20 vol. % hydrogen and 80 vol. % nitrogen was flowed though ammonia permeation tube (Commercially available from Valco Instruments Co.) and fed to the reactor at 1.4 L/min and 75 psig, resulting in about 100 ppmv ammonia in the reduction gas. The hydrogen flow rate was adjusted, depending on the [EB] to maintain a 1:2 ratio of hydrogen:hydrocarbon. The reduction temperature was ramped from 500° F. to 800° F. at 10° F./hr, held at 800° F. for fourteen hours, and allowed to cool to 625° F. The xylene isomerization results of the tests performed in this example are presented in Table 4 below.

TABLE 4

|  | Comparative Example 1 | Comparative Example 2 | Example 1 |
|---|---|---|---|
| $H_2$/EB Mole Ratio | 1.20 | 1.20 | 1.20 |
| Concentration of EB in Feed, wt. % | 8-10 | 11-12 | 11-12 |
| EB Conversion, % | 50.9 | 49.3 | 50.9 |
| Xylene Loss, % | 0.92 | 1.17 | ~0.2 |
| EB/XL | 65.6 | 44.4 | 200-300 |
| PXATE, % | 101.6 | 101.1 | 100.8 |

As illustrated in Table 4, the xylene loss that occurred during the xylene isomerization process was surprisingly much lower when the catalyst was reduced in the presence of both ammonia and hydrogen (Example 1) rather than in the presence of only hydrogen (Comparative Examples 1 and 2). The PXATE achieved by the catalyst reduced in the ammonia and the hydrogen was nearly equivalent to that achieved by the conventionally reduced catalysts. The results also demonstrate that the catalyst reduced in the presence of ammonia and hydrogen (Example 1) had a significantly higher xylene selectivity as indicated by the EB/XL ratio.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc. The various embodiments and components thereof disclosed herein may be used singularly or in combination with any other embodiment disclosed herein.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference herein is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A method of reducing xylene loss during isomerization of a paraxylene-depleted stream, comprising passivating a portion of acid sites on a zeolite isomerization catalyst by reducing the zeolite isomerization catalyst in the presence of a gas comprising a base and hydrogen, wherein the zeolite isomerization catalyst comprises a HZSM-5 zeolite support, a SSZ-57 zeolite support or combinations thereof and a Group VIII metal and wherein the base comprises ammonia, alkyl amines, hydrazine, or combinations thereof.

2. The method of claim 1, wherein the xylene loss occurs by one or more of the following reactions:

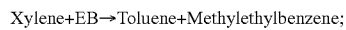

Xylene+EB→Toluene+Methylethylbenzene;

Xylene+EB→Benzene+Dimethylethylbenzene; or

Xylene+Xylene→Toluene+Trimethylbenzene, where EB represents ethylbenzene.

3. The method of claim 1, wherein the catalyst has a xylene selectivity expressed as the mole ratio of ethylbenzene conversion to xylene loss (EB/XL) of from about 70 to about 600.

4. The method of claim 1, wherein the catalyst has a xylene selectivity expressed as the mole ratio of ethylbenzene conversion to xylene loss (EB/XL) of from about 100 to about 450.

5. The method of claim 1, wherein the catalyst has a xylene selectivity expressed as the mole ratio of ethylbenzene conversion to xylene loss (EB/XL) of from about 150 to about 350.

6. The method of claim 1 having an initial PXATE about equal to or greater than 100%.

7. The method of claim 1 having an ethylbenzene conversion of from about 10 wt % to about 80 wt %.

8. The method of claim 1 having an ethylbenzene conversion of from about 20 wt % to about 75 wt %.

9. The method of claim 1 having an ethylbenzene conversion of from about 25 wt % to about 70 wt %.

10. The method of claim 1 having a xylene loss (XylLoss) during a continuous xylene isomerization run over a period of about 24 hours of from about 0.0 wt % to about 5.0 wt % at an ethylbenzene of about 50 wt %.

11. The method of claim 1 having a xylene loss (XylLoss) during a continuous xylene isomerization run over a period of about 24 hours of from about 0.1 wt % to about 3.0 wt % at an ethylbenzene of about 50 wt %.

12. The method of claim 1 having a xylene loss (XylLoss) during a continuous xylene isomerization run over a period of about 24 hours of from about 0.2 wt % to about 2.0 wt % at an ethylbenzene of about 50 wt %.

13. The method of claim 1 having a xylene loss (XylLoss) during a continuous xylene isomerization run over a period of about 24 hours of from about 0.2 wt % to about 1.0 wt % at an ethylbenzene of about 50 wt %.

14. The method of claim 1 having a xylene loss (XylLoss) during a continuous xylene isomerization run over a period of about 24 hours of from about 0.8 wt % to about 1.2 wt % at an ethylbenzene of about 50 wt %.

15. The method of claim 1 having a xylene loss (XylLoss) during a continuous xylene isomerization run over a period of about 4 weeks of from about 0.3 wt % to about 0.5 wt % at an ethylbenzene conversion of about 50 wt %.

16. The method of claim 1, wherein the base comprises ammonia formed in situ from nitrogen and hydrogen in the presence of the zeolite isomerization catalyst.

17. The method of claim 1, wherein the gas further comprises nitrogen.

18. The method of claim 1, wherein the Group VIII metal comprises platinum, palladium, nickel, or combinations thereof.

19. The method of claim 1, wherein the paraxylene-depleted stream comprises from about 0% to about 20% paraxylene based on the total weight of the stream.

20. The method of claim 1, wherein the paraxylene-depleted stream comprises from about 5% to about 25% ethylbenzene by total weight of the stream.

* * * * *